United States Patent [19]

Copping et al.

[11] 4,344,893
[45] Aug. 17, 1982

[54] PESTICIDE COMPOUNDS

[75] Inventors: Leonard G. Copping; John C. Kerry; Thomas I. Watkins; Robert J. Willis; Bryan H. Palmer, all of Nottingham, England

[73] Assignee: The Boots Company Limited, Nottingham, England

[21] Appl. No.: 124,183

[22] Filed: Feb. 25, 1980

Related U.S. Application Data

[63] Continuation-in-part of Ser. No. 15,011, Feb. 26, 1979, abandoned.

[30] Foreign Application Priority Data

Mar. 1, 1978 [GB] United Kingdom ................. 8002/78
Mar. 1, 1978 [GB] United Kingdom ................. 8003/78

[51] Int. Cl.$^3$ ................. C07C 143/68; C07C 133/04; C07C 133/08; C07C 143/74

[52] U.S. Cl. ..................... 260/456 A; 260/456 F; 260/455 A; 544/160; 544/159; 544/152; 544/145; 544/131; 544/130; 544/111; 544/85; 544/60; 544/59; 544/58.4; 546/325; 546/292; 546/284; 546/283; 546/262; 546/261; 546/225; 546/223; 546/222; 546/206; 546/189; 546/188; 549/72; 549/62; 549/60; 549/59; 560/17; 560/13; 564/251; 564/154; 564/151; 564/150; 564/149; 564/148; 564/81; 564/38; 564/36; 424/327; 424/323; 424/321; 424/303; 424/300; 424/285; 424/275; 424/274; 424/267; 424/263; 424/248.52; 424/248.5; 424/246; 548/557; 549/496

[58] Field of Search ........... 260/456 A, 456 F, 566 B, 260/455 A, 347.2, 326.84, 326.83, 326.82, 326.55, 326.5 SF; 560/27, 17, 13; 544/160, 159, 152, 145, 131, 130, 111, 85, 60, 59, 58.4; 546/325, 292, 284, 283, 262, 261, 225, 223, 222, 206, 189, 188; 549/72, 62, 60, 59; 564/251, 154, 151, 150, 149, 148, 81, 38, 36

[56] References Cited

U.S. PATENT DOCUMENTS 3,732,307  5/1973  Middleton ..................... 260/566 B
3,951,999  4/1976  Saunders et al. ............... 260/566 B

OTHER PUBLICATIONS

DeAmaral et al., J. Med. Chem., 12, 21 (1969).

Primary Examiner—Nicky Chan
Attorney, Agent, or Firm—Lawrence Rosen

[57] ABSTRACT

Novel compounds are described which are substituted benzophenone hydrazones. They have pesticidal activity, especially against insects and acarids, and pesticidal compositions and methods are described. Methods of making the compounds, and novel intermediates, are also described.

10 Claims, No Drawings

PESTICIDE COMPOUNDS

This application is a continuation-in-part of our application Ser. No. 15,011, filed Feb. 26, 1979, now abandoned.

This invention relates to compounds having pesticidal activity.

Commercially available insecticidal products generally fall into four main categories, namely chlorinated compounds such as DDT, camphechlor and BHC, organophosphorus compounds such as parathion, carbamates such as carbaryl and more recently synthetic pyrethroids such as permethrin.

Resistance to an insecticide often develops after a period of use and there is therefore always a need for new insecticides and particularly for new groups of insecticides.

Many proposals appear in the literature that a group of compounds has pesticidal properties, but often such compounds are found not to be commercially acceptable as pesticides.

We have now found that certain benzophenone hydrazones have insecticidal activity against a wide range of pests.

Certain benzophenone hydrazones are already known. For instance in U.S. Pat. No. 3,732,307 there are described compounds of the formula

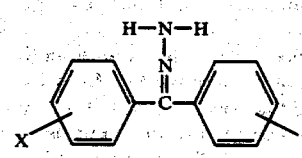

wherein
X is selected from the group consisting of perfluoroalkyl, perfluoroalkoxy and perfluoroalkylthio containing up to four carbon atoms, and
Y is selected from the group consisting of hydrogen, chlorine, bromine, fluorine, alkyl, alkoxy, alkylthio, perfluoroalkyl, perfluoroalkoxy and perfluoroalkylthio containing up to four carbon atoms.

These compounds are distinguished in that specification from, for example, benzophenone hydrazones described by J. R. DoAmaral et al., J. Med. Chem. 12, 21 (1969) apparently by virtue of, inter alia, having the hydrazine $NH_2$ unsubstituted in the compounds of U.S. Pat. No. 3,732,307. The compounds of that specification are described primarily as plant growth regulants although it is also mentioned in U.S. Pat. No. 3,732,307 that the compounds have activity against insects. Of the 24 Examples given in that specification 20 of the Examples are of compounds that contain neither alkylthio nor perfluoroalkylthio groups. The emphasis throughout the specification is primarily on compounds having perfluoroalkyl, especially trifluoromethyl, substitution and there is no suggestion that the class of compounds in which there is an alkylthio or perfluoroalkylthio in the 4-position of one of the benzene rings would be of any particular utility nor that compounds which are 4-substituted in this manner but additionally contain substituents other than those mentioned in that specification would be of any particular utility.

According to the invention there are provided compounds of formula I

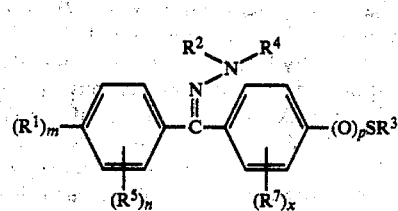

in which m is 0 and n is 0 or m is 1 and n is 0 or 1; p is 0, 2 or 3; x is 0 or 1; $R^1$, $R^5$ and $R^7$ are halogen, alkyl, haloalkyl or alkoxy or $R^1$ and an adjacent $R^5$ group together with the benzene to which they are attached form a naphthyl group; $R^2$ and $R^4$ may be the same or different and are hydrogen, alkyl, acyl, an ester group or optionally substituted carbamoyl or $R^2$ and $R^4$ together with the nitrogen which they are attached form a 5 to 7 membered ring which may optionally contain one or more heteroatoms; $R^3$ is optionally substituted alkyl, alkenyl, N,N-dialkylamino, or phenyl optionally substituted by alkyl or halogen; and with the proviso that when p is 0, $R^2$ and $R^4$ are not both hydrogen.

In one aspect of the invention p is 0, so that the substitution in one of the benzene rings is then $SR^3$ and the hydrazine $NH_2$ must be substituted. It is particularly surprising that the substitution of, for instance, $R^4$ by alkyl or, especially, acyl, ester or thioester or carbamoyl or thiocarbamoyl gives useful compounds.

According to another aspect of the invention p is 2 or 3. It will of course be appreciated that by referring to the substituent —$(O)_2SR^3$ we mean the substituent

and by referring to the substituent —$(O)_3SR^3$ we mean the substituent

The compounds where p is 3 are particularly preferred in the invention. It will further be appreciated that these substituents are entirely different from any substituents suggested in U.S. Pat. No. 3,732,307.

In the present specification any reference to halo or halogen should be construed as a reference to fluorine, chlorine, bromine or iodine, preferably fluorine, chlorine or bromine.

Preferred compounds within the first aspect of the invention include those wherein p, n, x=0, m=1, $R^1$ is halo, $R^2$ is hydrogen, $R^3$ is alkyl and $R^4$ is acyl or alkoxycarbonyl.

Preferred compounds within the second aspect of the invention include those wherein p=3, x=0, $R^2$ is hydrogen, $R^1$ and $R^5$ are halo, $R^4$ is hydrogen, acyl or alkoxycarbonyl and $R^3$ is alkyl, optionally substituted phenyl or optionally substituted benzyl.

In formula I, $R^1$, $R^5$ and $R^7$ are preferably halogen and especially chlorine. When one of these groups are alkyl or alkoxy these may be e.g. of 1 to 4 carbon atoms, but are preferably methyl or methoxy. It is generally preferred that m is 1, and n and x are 0. When they are haloalkyl this is preferably trifluoromethyl.

$R^2$ is preferably hydrogen and $R^4$ is preferably other than hydrogen and is usually a carbonyl derivative. When $R^2$ or $R^4$ are alkyl this may be e.g. of 1 to 4 carbon atoms and is preferably methyl. If $R^2$ or $R^4$ form a ring with the nitrogen to which they are attached this may be for example piperidine, pyrrolidine, thiamorpholine and especially morpholine.

If $R^2$ or $R^4$ is an ester group this is generally of formula $R^8XCO$, where X is oxygen or sulphur, preferably oxygen and $R^8$ is an organic radical e.g. alkyl, e.g. of 1 to 12, preferably 1 to 8 carbon atoms, and especially ethyl, these alkyl groups being optionally substituted, (e.g. by $C_{1-4}$ alkoxy; $C_{3-7}$ cycloalkyl; halogen or aryl, such as phenyl, substituted phenyl or naphthyl, aryloxy such as phenoxy and substituted phenoxy); cycloalkyl, e.g. of 3 to 7 carbon atoms and especially cyclopentyl; alkenyl e.g. of 2 to 12 carbon atoms, which group may optionally be substituted (e.g. by aryl such as phenyl or substituted phenyl); alkynyl e.g. of 2 to 6 carbon atoms; aryl such as optionally substituted phenyl or 2-naphthyl; furyl, thienyl, or pyridyl; and heterocyclyl such as morpholinyl, piperidyl and thiamorpholinyl. Where a phenyl group is substituted this may be by a wide number of groups e.g. $C_{1-4}$ alkyl, $C_{1-4}$ haloalkyl, nitro, $C_{1-4}$ alkoxy, $C_{1-4}$ alkylthio, $C_{1-4}$ dialkylamino, phenyl or halogen. If $R^2$ or $R^4$ are acyl this is generally of formula $R^9CO$ where $R^9$ is $R^8$ as defined above or hydrogen.

If $R^2$ or $R^4$, in Formula I, is a carbamoyl group, the group may be of the formula $-CONR^{10}R^{11}$ where $R^{10}$ and $R^{11}$ are the same or different and are hydrogen, optionally substituted alkyl or optionally substituted phenyl or together with the nitrogen to which they are attached form a 5 or 7 membered ring which may optionally contain one or more heteroatoms. Suitable optionally substituted alkyl or phenyl or heterocyclic groups are listed above in the description of, for instance, $R^2$, $R^4$ and $R^8$.

$R^3$ is preferably optionally substituted alkyl, e.g. of 1 to 4 carbon atoms. Preferred substituents are halogen. When $R^3$ is alkenyl this is usually 1-propenyl. When $R^3$ is dialkylamino this is preferably dimethylamino. It is particularly preferred that $R^3$ is methyl or trifluoromethyl.

A preferred group of compounds are those in which p is 3.

A particularly preferred group of compounds are those in which m is 1, n and x are 0, p is 3, $R^1$ is halogen, $R^3$ is $C_{1-4}$ alkyl, optionally substituted by halogen and $R^2$ is hydrogen.

Especially preferred from this group are compounds in which $R^3$ is methyl or trifluoromethyl and $R^4$ is $R^8(O)_qCO$ where q is 0 or 1, $R^8$ is $C_{1-12}$ alkyl, optionally substituted by $C_{1-4}$ alkoxy, $C_{3-7}$ cycloalkyl, halogen phenoxy or substituted phenoxy; $C_{3-7}$ cycloalkyl; $C_{2-12}$ alkenyl, optionally substituted by phenyl or substituted phenyl; $C_{2-6}$ alkynyl; or optionally substituted phenyl, wherein any substituted phenyl group is substituted by $C_{1-4}$ alkyl, $C_{1-4}$ haloalkyl, nitro, $C_{1-4}$ alkoxy, $C_{1-4}$ alkylthio, $C_{1-4}$ dialkylamino, phenyl or halogen; and when q is 0, $R^8$ is also hydrogen.

The compounds of the invention are active against a variety of economically important insects that cause serious and widespread damage to crops such as for example, insects of the order Lepidoptera including caterpillars of the diamond back month (*Plutella maculipennis*), the cabbage white butterfly (*Pieris brassicae*), The Egyptian cotton leaf worm (*Spodoptera littoralis*) and Heliothis spp. such as *H. armigera H. viriscens* and *H. zea*. Many of the compounds have also shown activity against other caterpillars such as these of the codling moth (*Laspeyresia pomonella*). Some of the compounds have shown activity against other pests such as beetles of the order Coleoptera, including the mustard beetle (*Phaedon cochleariae*), grain weevil (*Sitophilus granarius*), flour beetle (*Tribolium castaneum*) and mealworm (*Tenebrio molitor*); cockroaches of the order Orthoptera such as *Blatella germanica;* aphids of the order Hemiptera, including the vetch aphid (*Megoura viciae*).

Many of the compounds also have activity against a variety of economically important acarid and insect pests of animals, including farm livestock. For example, many compounds have been shown to be active against larvae stages of insects of the order Diptera e.g. sheep blowfly (Lucilia spp.) and mosquitoes e.g. *Aedes aegypti*. Some of the compounds especially those in which $R^4$ is a carbamoyl or thiocarbamoyl group have shown systemic activity i.e. the internal tissues of an animal which has been treated with the compound exert an insecticidal effect. This property is important in the treatment of animals such as cattle, which are infested with tissue-dwelling stages of insects e.g. warble fly (Hypoderma spp.). Some of the compounds are also active against lice and keds and acarid parasites especially ticks e.g. *Boophilus microplus* and mites e.g. Sacoptes spp.

Some of the compounds have also been shown to have fungicidal, herbicidal and plant-growth regulant activity.

The invention also includes an insecticidal composition comprising a compound of formula I and an inert diluent. More than one compound of the invention can be included in the composition, and the diluent can be a solid or liquid, optionally together with a surface-active agent for example a dispersing agent, emulsifying agent or wetting agent.

One or more additional pesticides such as for example compounds known to possess acaricidal or insecticidal activity can be added to the composition of the invention to enhance or widen the spectrum of its activity.

Such additional pesticides include, for example, an organophosphorus compound such as tetrachlorvinphos, fenitrothion, demeton-S-methyl, phosalone, dioxathion, chlorfenvinphos, dichlorvos, bromophosethyl, diazinon, dimethoate, methyl parathion, Bolstar[O-ethyl-O-(4-methylthiophenyl)-S-propyl phosphorodithioate], or chlorpyrifos; a carbamate such as methomyl, carbaryl; pirimicarb or promecarb; a bridged diphenyl compound such as tetradifon, tetrasul or DDT; a chlorinated hydrocarbon such as benzene hexachloride, endosulphan, endrin or toxaphene; an acaricide such as amitraz, chlordimeform, clenpyrin, chlormethiuron or nimidane; a synthetic pyrethroid such as permethrin, fenvalerate or cypermethrin or a thin pesticide such as cyhexatin or fenbutatin oxide.

The composition of the invention can take any of the forms known for the formulation of insecticidal compounds, for example, it can be in the form of a solution, an aqueous dispersion, an aqueous emulsion, an emulsifiable concentrate, a dispersible powder, a dusting powder or granules. Thus it can be in a suitable form for direct application as an insecticide or as a concentrate requiring dilution with an appropriate quantity of water or other diluent before application.

As a dispersion the composition comprises a compound of the invention dispersed in an aqueous medium.

It is often convenient to supply the consumer with a concentrate which when diluted with water forms a dispersion of the desired concentration and can be provided in, for example, any of the following forms. It can be a dispersible solution which comprises a compound of the invention dissolved in a water-miscible solvent with the addition of a dispersing agent, or a dispersible powder comprising a compound of the invention and a dispersing agent. A further alternative comprises a compound of the invention in the form of a finely ground powder in association with a dispersing agent and intimately mixed with water to give a paste or cream which can if desired be added to an emulsion of oil in water to give a dispersion of active ingredient in an aqueous oil emulsion.

An emulsion comprises a compound of the invention dissolved in a water-immiscible solvent which is formed into an emulsion with water in the presence of an emulsifying agent. An emulsion of the desired concentration can be formed from a concentrated stock emulsion that comprises a compound of the invention in combination with an emulsifying agent, water and water-immiscible solvent. Alternatively the consumer can be supplied with an emulsifiable concentrate comprising a solution of a compound of the invention in a water-immiscible solvent containing an emulsifying agent.

A dusting powder comprises a compound of the invention intimately mixed and ground with a solid pulverulent diluent, for example, kaolin.

A granular solid comprises a compound of the invention associated with similar diluents to those employed in dusting powders but the mixture is granulated by known methods. Alternatively the active ingredient can be absorbed or adsorbed on a pre-formed granular diluent for example fuller's earth, attapulgite or limestone grit.

The concentration of the active ingredient (when used as the sole active component) in a composition for direct application to the crop by conventional ground methods is preferably within the range of 0.001 to 10 percent by weight of the composition, especially 0.005 to 5 percent by weight, but more concentrated compositions containing up to 20 percent may be desirable in the case of aerial sprays. As a concentrated primary composition the concentration of active ingredients may vary widely and can be, for example, from 5 to 95 percent by weight of the composition.

As previously described the compounds of the invention have exceptional activity as insecticides and accordingly the invention includes a method of combating insects which comprises applying a compound of formula I to the locus of the insects, that is, the insects or their habitat. The compound of the invention can either be applied on its own or more preferably as one of the compositions described above.

Many of the insects which the compounds of the invention are active against, for example those of the order Lepidoptera and Diptera, attack plant life and a preferred method of the invention is one of protecting plants from attack by insects by applying a compound of formula I to the locus of the plants. For instance the diamond back moth and cabbage white butterfly attack vegetable crops such as brassicas, and leaf worms are a serious pest on cotton.

Direct treatment by for example spraying or dusting the plants infested with insects is often the preferred method but the active compound can also be applied to the soil in which plants are grown as granules, or as a root drench. In such instances the active compound is absorbed by the roots of the plant and confers protection from the insects. The quantity of active compound applied can vary widely depending on the particular circumstances and usually the amount is in the range of from 0.01 to 20 kilogram per hectare, more especially, from 0.1 to 10 kilogram per hectare.

Also included in the invention is a method of protecting animals from attack by pests which comprises treating the animal with a compound of formula I. Parasites are a frequent source of irritation to animals such as livestock and many can be controlled by external application of a compound of formula I. The method may be by direct application to the animal, or by application to the quarters, e.g. buildings, in which the animals live.

The compounds of the invention can be prepared by a number of processes, as follows:

(1) By reacting a compound of formula II

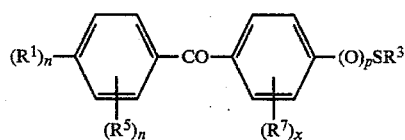

With a compound of formula $NH_2NR^2R^4$. When $R^2$ and $R^4$ are both hydrogen the product can then be acylated with (a) an acyl halide or acid anhydride when $R^2$ or $R^4$ is to be an acyl group, with (b) a chloroformate or chlorothioformate when $R^2$ or $R^4$ is to be an ester group, or with (c) an isocyanate or isothiocyanate when $R^2$ or $R^4$ is to be a carbamoyl or thiocarbamoyl group.

In this specification it will be appreciated that the term "acylating agent" includes these three types of compound.

The reaction with the hydrazine or hydrazine derivative is usually carried out at a temperature of from 50° C. to 100° C, in the presence of acetic acid.

The acylation reaction is preferably carried out in the presence of an inert organic liquid as the reaction medium which is also preferably a solvent for the reactants, at a temperature of from 0° C. to 100° C. Advantageously the reaction is effected in the presence of a suitable acid-binding agent, for example a tertiary alkyl amine, pyridine or an alkali metal carbonate. When the acylating agent is a halide this is preferably the chlorine.

Compounds of formula II in which p is 3 are novel and can be prepared by reacting a sulphonyl halide of the formula $R^3SO_2X$ where X is halogen and preferably chlorine, with the corresponding 4'-hydroxy compound of formula III

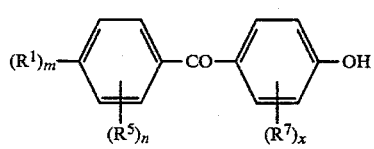

This step is preferably carried out in the presence of an inert organic solvent and an acid binding agent.

Compounds of formula II in which p is 0 can be prepared by a Friedel-Craft reaction between

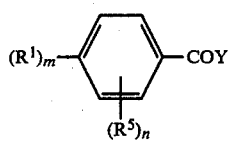

where Y is a halide, usually chloride, with

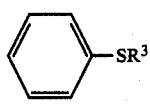

Compounds of formula II in which p is 2 may be prepared by oxidising e.g. with hydrogen peroxide, the corresponding compound in which p is 0

(2) When p is 3, by reacting a compound of formula IV

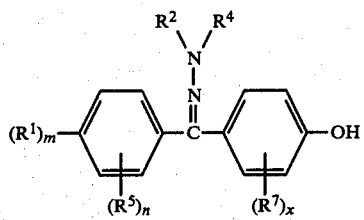

in which $R^2$ and $R^4$ are not both hydrogen, with a compound of formula $RSO_2Y$ in which Y is halogen, preferably chlorine. The reaction is preferably carried out at a temperature of 0° to 100° C., usually in the presence of an acid binder Compounds of formula IV can, in their turn, be prepared by reacting a suitable hydrazine derivative of the formula $NH_2NR^2R^4$ with a compound of formula III above, preferably in the presence of an inert organic solvent and optionally together with acetic acid. Compounds of formula IV in which $R^2$ and $R^4$ are not both hydrogen are novel reactants and are included as part of the present invention.

The present state of our knowledge indicates that most of the above reactions give rise to a product that comprises a mixture of the E and Z-isomers.

It is to be understood that formula I above denoting the compounds of the invention includes both of these isomers. In all cases the pairs of isomers can be separated by conventional methods, such as for example chromatography or fractional recrystallisation, but, as the isomeric mixtures have very valuable insecticidal activity, we generally find that there is no advantage in separating the isomers. The activity of the isomers of any one compound may differ and in some cases the activity of one isomer may be negligible; pure isomers lacking insecticidal activity form no part of the present invention. The novel reactants of formula IV also exist in isomeric form and the structure shown is intended to include both of the isomers.

The invention is illustrated in the following Examples.

Compounds according to the invention were prepared according to one of the following reaction schemes.

Scheme 1

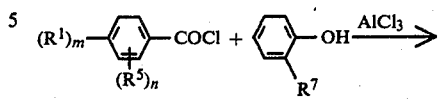

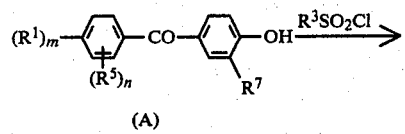

(A)

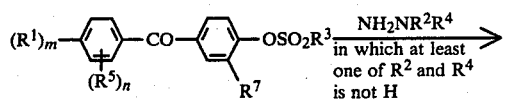

(B)

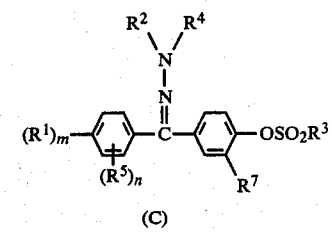

(C)

Scheme 2

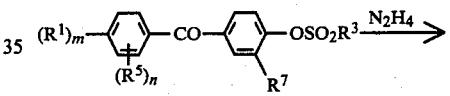

(B) from Scheme 1

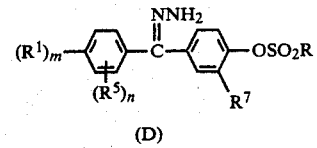

(D)

Scheme 3

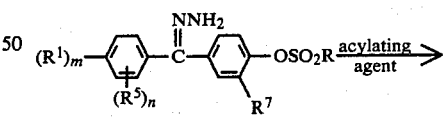

(D) from Scheme 2

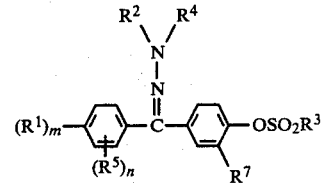

(C) from Scheme 1

Scheme 4

-continued

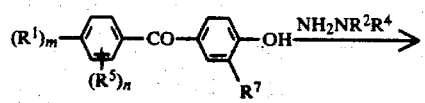

(A) from Scheme 1

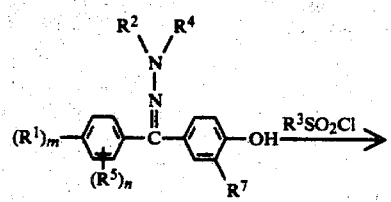

(E)

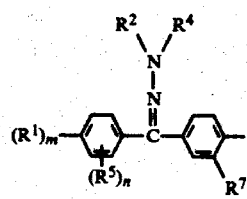

(C) from Scheme 1

Scheme 5

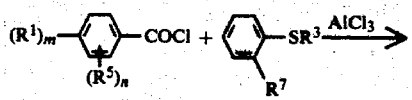

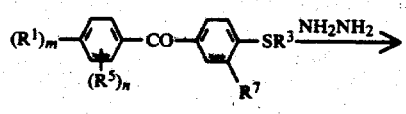

(F)

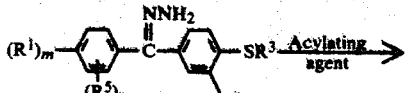

(G)

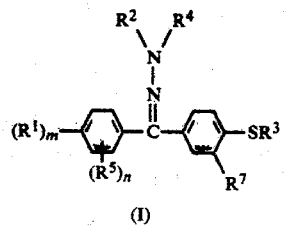

(I)

Scheme 6

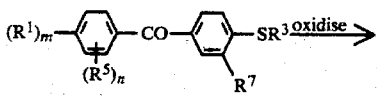

(F) from Scheme 5

-continued

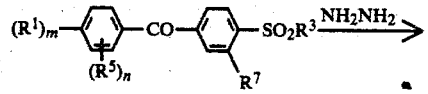

(J)

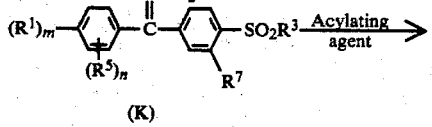

(K)

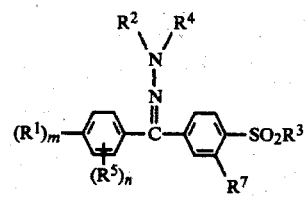

(L)

Scheme 7

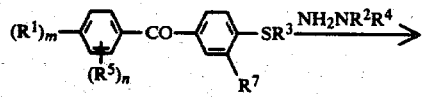

(F) from Scheme 5

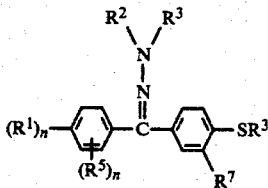

(I) from Scheme 5

By the term "acylating agent" is included acid halides, acid anhydrides, isocyanates and isothiocyanates.

Examples 1 to 7 are typical examples of preparations according to these schemes.

Structures of all compounds prepared according to the invention were confirmed by infra-red analyses.

EXAMPLE 1

Illustration of Scheme 1

Phenol is reacted with p-chlorobenzoyl chloride in a Friedel-Crafts reaction in the presence of aluminium chloride to give 4-chloro-4'-hydroxybenzophenone, 179°-181° C. (A). To a solution of this (5 g.) in pyridine (6 ml.) was added methanesulphonyl chloride (2.5 g.), at room temperature. The reactants were heated on a steam bath for 1½ hours and the liquid reaction product poured into dilute hydrochloric acid to give a solid which was filtered and air-dried. This solid was recrystallised from industrial methylated spirits to give 4-chloro-4'-methylsulphonyloxybenzophenone, m.p. 120°-121° C. (B). A solution of 9.4 g. of this product and ethyl carbazate (7.8 g.) in glacial acetic acid (8 ml.) and ethanol (200 ml.) was heated under reflux for 48 hours and then evaporated to dryness in vacuo. The residue was extracted with methylene chloride (250 ml.) and the extract washed with water, aqueous sodium hydroxide (2.5 N) and water and then dried and evaporated to dryness to give 4-chloro-4'-methylsulphonyloxybenzophenone ethoxycarbonylhydrazone, m.p. 132.5°–140° C. (C).

EXAMPLE 2

Illustration of Scheme 2

To a solution of (B) from Example 1 (9.35 g.) in ethanol (200 ml.) was added hydrazine hydrate (8 ml.) followed by glacial acetic acid (1.5 ml.). The mixture was heated under reflux with stirring for 17 hours. The solvent was evaporated under reduced pressure to give an oil which was extracted with chloroform. The extract was washed with water, aqueous sodium hydroxide and water and then dried over magnesium sulphate. The solvent was evaporated under reduced pressure to give an oil. On standing this crystallised to give 4-chloro-4'-methylsulphonyloxybenzophenone hydrazone, m.p. 70°–110° C. (D).

EXAMPLE 3

Illustration of Scheme 3

A solution of propionyl chloride (2 g.) in ether (15 ml.) was added dropwise with stirring to a solution of (D) from Example 2 (6.2 g.) in pyridine (20 ml.) at 0° to 5° C. over 30 minutes. The mixture was then stirred at room temperature for 1½ hours and then quenched with water (1 liter) and the solid filtered, washed with dilute hydrochloric acid and water and dried in vacuo at 60° C. for 1½ hours to give 4-chloro-4'-methylsulphonyloxybenzophenone propionylhydrazone m.p. 128° to 144° C (C).

EXAMPLE 4

Illustration of Scheme 4

A solution of A from Example 1 (92.8 g.), ethyl carbazate (100 g.) glacial acetic acid (100 ml.) in ethanol (1 liter) was heated under reflux, with stirring, for 48 hours. Evaporation of solvent under reduced pressure gave a slurry and the solid was separated from the liquors by filtration. This solid was washed with a little cold industrial methylated spirit and then dried in vacuo at 50° C.

The liquors were evaporated again under reduced pressure and the resulting oil was extracted with chloroform and the extract washed with aqueous sodium carbonate and then water. The extract was dried over magnesium sulphate and evaporated under reduced pressure to give a second batch of solid.

The combined solid material was recrystallised from industrial methylated spirits to give 4-chloro-4'-hydroxybenzophenone ethoxycarbonylhydrazone, m.p. 185°–187° C. (E). To a solution comprising (E) (95.55 g.) and triethylamine (90 ml.) in tetrahydrofuran (700 ml.) was added dropwise methanesulphonyl chloride (44.7 g.) in tetrahydrofuran (25 ml.) over 35 minutes. A fine precipitate formed with evolution of heat and the mixture was left overnight with continuous stirring. It was poured into water (500 ml.) and then extracted with methylene dichloride (500 ml.). The extract was washed with five 500 ml. portions of water and then dried with magnesium sulphate. Evaporation of solvent under reduced pressure gave a semi-solid residue which was triturated with industrial methylated spirits, filtered and washed with further solvent, leaving a white solid which was dried in vacuo at 75° C. for three hours, to give 4-chloro-4'-methylsulphonyloxybenzophenone ethoxycarbonylhydrazone, m.p. 132°–142° C. (C).

EXAMPLE 5

Illustration of Scheme 5

Isopropylphenyl sulphide was reacted with 4-chlorobenzoyl chloride in a Friedel-Crafts reaction in the presence of aluminium chloride to give 4-chloro-4'-isopropylthiobenzophenone, m.p. 105°–107° C. (F). To a solution of (F) (101 g.) in ethanol (650 ml.) was added hydrazine hydrate (67.5 ml.). The mixture was heated under reflux for 24 hours, after which the solvent was evaporated under reduced pressure. Water was added to the residue which was extracted with chloroform, washed with aqueous sodium hydroxide and then water. The organic extract was dried with magnesium sulphate and evaporated under reduced pressure to give 4-chloro-4'-isopropylthiobenzophenone hydrazone, b.p. 188°–190° C. at 0.1 mm. (G). This was then treated in a similar manner to that described in Example 3 with ethyl chloroformate to give 4-chloro-4'-isopropylthiobenzophenone ethoxycarbonylhydrazone, m.p. 115°–135° C. (H).

EXAMPLE 6

Illustration of Scheme 6

Using a Friedel-Crafts reaction as described in Example 5 there was obtained 4-chloro-4'-propylthiobenzophenone, m.p. 94°–95° C. (F). This (2.9 g.) was then dissolved in glacial acetic acid and hydrogen peroxide added (3.5 ml. of 100 vol.). The mixture was stirred and heated at 60° C. for 5 hours and then poured into water. The solid product was collected washed with water, dried and recrystallised from ethanol to give 4-chloro-4'-propylsulphonylbenzophenone, m.p. 140.5°–142.5° C. (I). This was then treated with hydrazine hydrate as described in Example 5 to give 4-chloro-4'-propylsulphonylbenzophenone hydrazone, m.p. 110°–120° C. (J) which was then treated with propionyl chloride in a similar manner to that described in Example 3 to give 4-chloro-4'-propylsulphonylbenzophenone propionylhydrazone, m.p. 155°–170° C. (K).

EXAMPLE 7

Illustration of Scheme 7

A solution of (F) from Example 5 (14.52 g) was treated with ethyl carbazate in a similar manner to that described in Example 1 to give 4-chloro-4-isopropylthiobenzophenone ethoxycarbonylhydrazone, m.p. 115°–135° C.

In the above and with the following Examples the products are generally obtained as mixtures of geometric isomers, the ratio of the two isomers varying from product to product.

EXAMPLES 8–267

The compounds shown in the following Table were prepared by one of the schemes given above in a similar manner to the method described above in the appropriate Example.

The physical data (melting point in °C., unless otherwise stated) are given in column J for the final product, in column K for the starting material and in column L for the intermediate.

When using Scheme 3 the starting material is the product of a previous Example.

The starting material (column K) is type A when Schemes 1, 2 or 4 are used and type F if Schemes 5 or 7 are used.

The intermediate (column L) is type B if Schemes 1 or 2 are used, type E if Scheme 4 is used and type G if Scheme 5 is used.

In the column headed A there is given the type of acylating agent or hydrazine derivative used as follows:

Acylating Agents

| | |
|---|---|
| M | = Acyl halide |
| N | = Acid anhydride |
| N' | = Acetic-formic anhydride |
| O | = Methyl isocyanate |
| P | = Phenyl isocyanate |
| Q | = Methyl isothiocyanate |
| MM | = p-Chlorophenyl isocyanate |
| NN | = Ethyl isocyanate |
| OO | = t-butyl isocyanate |
| PP | = butyl isocyanate |
| QQ | = propyl isocyanate |
| N" | = phthalic anhydride |
| RR | = 2-chloroethyl isocyanate |
| MA | = β-butyrolactone |
| MB | = ethyl oxalyl chloride |
| MC | = ethyl fluoroacetate |
| MD | = isopropyl isocyanate |
| ME | = trichloracetyl isocyanate |

Hydrazine derivatives

| | |
|---|---|
| S | = Ethyl carbazate |
| T | = Methyl carbazate |
| U | = Semicarbazide |
| V | = Benzyl carbazate |
| W | = N-aminomorpholine |
| X | = Thiosemicarbazide |
| Y | = 4,4-Dimethylsemicarbazide |
| Z | = N-carbazoyl morpholine |
| SS | = 2-carbazoyl-2-methoxypropane |
| TT | = 2-carbazoylethanol |
| UU | = 2-carbazoylpropan-2-ol |
| VV | = aminopiperidine |
| WW | = 2,2,2-trichloroethyl carbazate |
| XX | = oxamoyl hydrazine |
| YY | = IH,IH-heptafluorobutyl carbazate |
| ZZ | = 3-amino-2-oxo-oxazolidine |
| SA | = 2,2,2-trifluoroethyl carbazate |
| SB | = 2-methylsemicarbazide |

The column headed B identifies the scheme used.

The column headed C identifies the Example from which starting material is derived.

In the Table

| | |
|---|---|
| ND | = not determined. |
| * | = Starting material prepared by reacting product of Example 2 with methylhydrazine to give crude 4-chloro-4-methylsulphonyl oxybenzophenone methylhydrazone. |

+ = L was obtained by diazotizing 4-amino-4'-chlorobenzophenone and treating with sulphur dioxide to give the sulphonyl chloride derivative (m.p. 113–114° C.) which was then reacted with the appropriate dialkylamine

| Ex. No. | R¹ | R⁵ | R⁶ | R³ | p | R⁷ | R² | R⁴ | J | K | L | A | B | C |
|---|---|---|---|---|---|---|---|---|---|---|---|---|---|---|
| 8 | Cl | H | H | Pr | 3 | H | H | —COOEt | 112–136 | 179–181 | 185–190 | s | 4 | |
| 9 | Br | H | H | Me | 3 | H | H | —COOEt | 151.5–158 | 187.5–191 | 135–136.5 | s | 1 | |
| 10 | F | H | H | Me | 3 | H | H | —COOEt | 167.5–169 | 169.5–171.5 | 110–111 | s | 1 | |
| 11 | Cl | H | H | Et | 3 | H | H | H | 99.5–100 | 179–181 | 99.5–100 | M | 2 | |
| 12 | Cl | H | H | Me | 3 | H | H | —COPr | 138–154 | | | s | 3 | 2 |
| 13 | Me | H | H | Me | 3 | H | H | —COOEt | 117–119 | 171–173 | 88.5–91 | M | 1 | 2 |
| 14 | Cl | H | H | Me | 3 | H | H | —COBu | 115–147 | | | M | 3 | 2 |
| 15 | Cl | H | H | Me | 3 | H | H | —COMe | 148–159 | | | M | 3 | 2 |
| 16 | MeO | H | H | Me | 3 | H | H | —COOEt | 120–130 | 114.5–145.5 | 146.5–149.5 | s | 1 | |
| 17 | Cl | H | H | Me | 3 | H | H | —COCH₂OMe | 144–146.5 | | | M | 3 | 2 |
| 18 | Cl | H | H | Me | 3 | H | H | —COPh | 174–178 | | | M | 3 | 2 |
| 19 | Cl | H | H | Me | 3 | H | H | —CO(CH₂)₂CH=CH₂ | 138–148 | | | M | 3 | 2 |
| 20 | Cl | H | H | Me | 3 | H | H | —CO-cyclopropyl | 158–167 | | | M | 3 | 2 |
| 21 | Cl | H | H | Me | 3 | H | H | —COOPr | 127–145 | | | M | 3 | 2 |
| 22 | Cl | H | H | 4-Me-C₆H₄ | 3 | H | H | —COOEt | 90–115 | 179–181 | 185–190 | s | 4 | |
| 23 | Cl | H | H | Me | 3 | H | H | —COC₅H₁₁ | 122–132 | | | M | 3 | 2 |
| 24 | Cl | H | H | Me | 3 | H | H | —COSEt | 156–172 | | | M | 3 | 2 |
| 25 | Cl | H | H | Et | 3 | H | H | —COPr | 112–119 | | | M | 3 | 2 |
| 26 | Cl | H | H | Et | 3 | H | H | —COBu | 105–125 | | | M | 3 | 2 |
| 27 | Cl | H | H | ClCH₂— | 3 | H | H | —COOEt | 110–130 | 179–181 | 185–190 | s | 4 | |
| 28 | Cl | H | H | Me | 3 | H | H | —COC₈H₁₇ | 134–137 | | | M | 3 | 2 |
| 29 | Cl | H | H | Me | 3 | H | H | —COC₆H₁₃ | 118–133 | | | M | 3 | 11 |
| 30 | Cl | H | H | Et | 3 | H | H | —COOPr | 120–124 | | | M | 3 | 11 |
| 31 | Cl | H | H | Me | 3 | H | H | —COOEt | 159–161 | | | M | 3 | 2 |
| 32 | Cl | H | H | Me | 3 | H | H | —CO-C₆H₄-OMe | 147–149 | | | M | 3 | 2 |
| 33 | Cl | H | H | Me | 3 | H | H | —COPrⁱ | 145–151 | | | M | 3 | 2 |
| 34 | H | H | H | Me | 3 | H | H | —COBuⁱ | 74–83 | | | M | 2 | 2 |
| 35 | H | H | H | Me | 3 | H | H | H | 111–126 | | 102.5–104.5 | s | 3 | 3 |
| 36 | H | H | H | Me | 3 | H | H | —COPr | 95–125 | ND | | M | 3 | 34 |
| 37 | Cl | H | H | Me | 3 | H | H | —COOEt | 175–178 | | | M | 3 | 34 |
| 38 | Cl | H | H | Me | 3 | H | H | —CO-C₆H₄-OEt | 150–185 | 179–181 | 71–73 | M | 3 | 2 |
| 39 | Cl | H | H | Pr | 3 | H | H | —COOPrⁱ | 86.5–93 | | | s | 2 | |

-continued

| Ex. No. | R$^1$ | R$^5$ | R$^6$ | R$^3$ | P | R$^7$ | R$^2$ | R$^8$ | J | K | L | A | B | C |
|---|---|---|---|---|---|---|---|---|---|---|---|---|---|---|
| 40 | Cl | H | H | Me | 3 | H | H | —CO— (tetrahydrofuranyl) | 160–173 | | | M | 3 | 2 |
| 41 | Cl | H | H | Me | 3 | H | H | —COC$_7$H$_{15}$ | 133–133 | | | M | 3 | 2 |
| 42 | Cl | H | H | Me | 3 | H | H | —COCHClMe | 145–147 | | | M | 3 | 2 |
| 43 | Cl | H | H | Bu | 3 | H | H | —COOEt | 116–118 | | | S | 4 | |
| 44 | Cl | H | H | Me | 3 | H | H | —COOC$_5$H$_{11}$ | 115–122 | | | M | 3 | 2 |
| 45 | Cl | H | H | Me | 3 | H | H | —COOC$_8$H$_{17}$ | 160–173 | | | M | 3 | 2 |
| 46 | Cl | Cl | H | Me | 3 | H | H | —CO— (4-chlorophenyl) | 168–178 | 158.5–170 | 85.5–86.5 | S | 1 | |
| 47 | Br | H | H | Me | 3 | Cl | H | —COOEt | 171–181 | 52.5–53.5 | 79–80 | S | 1 | |
| 48 | Cl | H | H | Me | 3 | Me | H | —COOEt | 110–113 | 187.5–191 | 135–136.5 | S | 2 | |
| 49 | Cl | H | H | Me | 3 | H | H | —COOEt | 131–140 | 211–211.5 | 90–91 | S | 1 | |
| 50 | Cl | H | H | C(CH$_2$)$_3$ | 3 | H | H | H | 109–116 | 179–181 | 185–190 | S | 4 | |
| 51 | Cl | H | H | Me | 3 | H | H | —COOEt | 150–161 | | | M | 3 | 2 |
| 52 | Cl | H | H | Me | 3 | H | H | —CO— (cyclopentyl) | 173–182 | | | M | 3 | 2 |
| 53 | Cl | H | H | Me | 3 | H | H | —COOPh | 133–153 | | | M | 3 | 2 |
| 54 | Br | H | H | Me | 3 | H | H | —COPr | 154–157.5 | | | M | 3 | 48 |
| 55 | Cl | Br | H | Me | 3 | H | H | —COBu | 140–144 | | | M | 3 | 48 |
| 56 | Br | H | H | ClCH$_2$— | 3 | H | H | —COOEt | 129.5–130.5 | 187.5–191 | 200.5–203 | S | 4 | |
| 57 | Cl | Br | H | Me | 3 | H | H | —COOEt | 193–194 | 193–194 | 89.5–92 | S | 1 | |
| 58 | Br | H | H | Me | 3 | H | H | —CO— (cyclopropyl) | 177–180 | | | M | 3 | 48 |
| 59 | Cl | I | H | Me | 3 | H | H | —COOEt | 164–168 | 191–192 | 82–85 | S | 1 | |
| 60 | Cl | H | H | Me | 3 | H | H | —COC(Me$_2$)Pr | 130–140 | | | M | 3 | 2 |
| 61 | Et | H | H | Me | 3 | H | H | —CONHMe | 186–188 | | | O | 3 | 2 |
| 62 | Br | Br | H | Me | 3 | H | H | —COOEt | 142–147 | 99–100 | 88–89 | S | 1 | |
| 63 | Cl | H | H | Me | 3 | H | H | —CONH$_2$ | 97–103 | | | U | 1 | |
| 64 | Br | H | H | Me | 3 | H | H | —COOBu | 121–125 | | | M | 3 | 2 |
| 65 | Cl | H | H | Me | 3 | H | H | —COCH$_2$CH(Me)Et | 128–131 | 187.5–191 | 135–136.5 | M | 3 | 2 |

-continued

| Ex. No. | R¹ | R⁵ | R⁶ | R³ | p | R⁷ | R² | R⁴ | J | K | L | A | B | C |
|---|---|---|---|---|---|---|---|---|---|---|---|---|---|---|
| 66 | Cl | H | H | Me | 3 | H | H | —CO—⟨C₆H₄-Cl⟩ | 139–146 | | | M | 3 | 2 |
| 67 | Cl | H | H | Me | 3 | H | H | —COCHCl₂ | 139–141 | | | M | 3 | 2 |
| 68 | Cl | H | H | Me | 3 | H | H | —COCHC₈H₁₇ | 95–97 | | | M | 3 | 2 |
| 69 | Cl | H | H | Me | 3 | H | H | —COOC₈H₁₇ | 150–162 | | | M | 3 | 2 |
| 70 | Cl | H | H | ⟨C₆H₄-Cl⟩ | 3 | H | H | —CO—⟨cyclohexyl⟩ | | | | S | 4 | |
| 71 | Cl | H | H | Me | 3 | H | H | —COOEt | 157–160 | 179–181 | 185–190 | M | 3 | 2 |
| 72 | Cl | H | H | Me | 3 | H | H | —CO—⟨C₆H₄-F⟩ | 180–186 | | | M | 3 | |
| 73 | Cl | H | H | Me | 3 | H | H | —CO—⟨C₆H₄-F⟩ | 166–169 | | | M | 3 | 2 |
| 74 | OMe | H | H | Me | 3 | H | H | —CO—⟨C₆H₄-Me⟩ | 182–186 | | | M | 3 | |
| 75 | Cl | Cl | H | Me | 3 | H | H | —COOEt | 184–188 | 167–168 | 125–127 | S | 1 | 2 |
| 76 | SMe | H | H | Me | 3 | H | H | —CONH₂ | 144–148 | 179–181 | 120–121 | U | 1 | 2 |
| 77 | Cl | H | H | Me | 3 | H | H | —COOEt | 114–118 | 133–134 | ND | S | 3 | |
| | | | | | | | | | 158–174 | | | M | 3 | |
| 78 | Cl | H | H | Me | 3 | H | H | —CO—⟨C₆H₄-Cl⟩ | 89–97 | | | M | 3 | 2 |
| 79 | Cl | H | H | Me | 3 | H | H | —COOC₇H₁₅ | 166–168 | | | M | 3 | 2 |
| 80 | Cl | H | H | Me | 3 | H | H | —CO—⟨C₆H₄-Me⟩ | 128–129.5 | | | M | 3 | 2 |
| 81 | Cl | H | H | Me | 3 | H | H | —CO—⟨C₆H₄-Me⟩ | 156–158 | | | M | 3 | 2 |
| 82 | Me | Cl | H | Me | 3 | H | H | —COOEt | 150–165 | 153–154 | 136–137 | S | 1 | |
| 83 | Cl | H | H | CF₃ | 3 | H | H | —CO—⟨C₆H₄-NO₂⟩ —COOEt | 94–122 | 179–181 | 185–190 | S | 4 | |

-continued

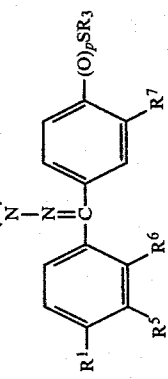

| Ex. No. | R¹ | R⁵ | R⁶ | R³ | p | R⁷ | R² | R⁴ | J | K | L | A | B | C |
|---|---|---|---|---|---|---|---|---|---|---|---|---|---|---|
| 84 | Cl | H | H | Me | 3 | H | H | —COBu$^i$ | 115–132 | | | M | 3 | 2 |
| 85 | Cl | H | H | Me | 3 | H | H | —COOBu$^i$ | 105–127 | | | M | 3 | 2 |
| 86 | Cl | H | H | Me | 3 | H | H | —COC$_{11}$H$_{23}$ | 102–132 | | | M | 1 | |
| 87 | Cl | H | H | Me | 3 | F | H | —COOEt | 138–144 | | | S | 3 | |
| 88 | Cl | H | H | Me | 3 | H | H | —COOEt | 173–175 | | | M | 3 | 2 |
| 89 | Cl | H | H | Me | 3 | H | H | —CO—C$_6$H$_4$-Br | 150–156 | | | M | 3 | 2 |
| 90 | Cl | H | H | Me | 3 | H | H | —CO-cyclobutyl | 143–145 | | | M | 3 | 2 |
| 91 | Cl | H | H | Me | 3 | H | H | —COCH$_2$OPh | 177–178 | | | M | 3 | 2 |
| 92 | Cl | H | H | Me | 3 | H | H | —CO-cyclopentyl | 151–167 | | | M | 3 | 2 |
| 93 | Cl | H | H | Pr$^i$ | 3 | H | H | —COO-C$_6$H$_4$-OMe | 104–107 | 179–181 | 185–190 | S | 4 | |
| 94 | Cl | H | H | Me | 3 | H | H | —CO-C$_6$H$_3$-Cl$_2$ | 185–186.5 | | | M | 3 | 2 |
| 95 | Cl | H | H | Me | 3 | H | H | —CO-C$_6$H$_4$-Bu$^t$ | 161.5–164 | | | M | 3 | 2 |
| 96 | Cl | Cl | H | Me | 3 | H | H | H | Oil | 134–135 | 119–120 | S | 2 | |
| 97 | Cl | H | H | NMe$_2$ | 3 | H | H | —COOEt | 135–140 | 179–181 | 185–190 | S | 4 | |
| 98 | Cl | H | H | Me | 3 | H | H | —CO-C$_6$H$_4$-F | 174–178 | | | M | 3 | 2 |
| 99 | Cl | H | H | Me | 3 | H | H | —CO-C$_6$H$_4$-Me | 167–170 | | | M | 3 | 2 |
| 100 | Cl | H | H | Me | 3 | H | H | —CO-thienyl | 157–158 | | | M | 3 | 2 |
| 101 | Cl | H | H | Me | 3 | H | H | —COC$_9$H$_{19}$ | 126–132 | 179–181 | 185–190 | M | 3 | 2 |
| 102 | Cl | H | H | BrCH$_2$ | 3 | H | H | —COOEt | 138–143 | | | S | 4 | |
| 103 | Cl | H | H | Me | 3 | H | H | —CO(CH$_2$)$_8$CH=CH$_2$ | 105–115 | | | M | 3 | 2 |

-continued

[Structure: R²(R⁴)N-N=C(R⁶-phenyl-R⁵-R¹)(R⁷-phenyl-(O)ₚSR₃)]

| Ex. No. | R¹ | R⁵ | R⁶ | R³ | p | R⁷ | R² | R⁴ | J | K | L | A | B | C |
|---|---|---|---|---|---|---|---|---|---|---|---|---|---|---|
| 104 | Cl | H | H | Me | 3 | H | H | —CO—⟨⟩—⟨⟩ | 210–212 | | | M | 3 | 2 |
| 105 | Cl | H | H | Me | 3 | H | H | —COOC₁₂H₂₅ | 86–100 | | | M | 3 | 2 |
| 106 | Cl | H | H | Me | 3 | H | H | —CHO | 197–198 | | | N' | 3 | 2 |
| 107 | Cl | H | H | Me | 3 | H | H | —COOCH₂CH=CH₂ | 115–121 | | | M | 3 | 2 |
| 108 | Cl | H | H | Me | 3 | H | H | —CO—⟨⟩—Me (Me) | 135–140 | | | M | 3 | 2 |
| 109 | Cl | H | H | Me | 3 | H | H | —CO—⟨⟩—Pr | 148–151.5 | | | M | 3 | 2 |
| 110 | Cl | H | H | Me | 3 | H | H | —CO—⟨⟩—Et | 176–178 | | | M | 3 | 2 |
| 111 | Cl | H | H | Me | 3 | H | H | —CO—⟨⟩(Br, Br) | 132–134 | | | M | 3 | 2 |
| 112 | Cl | H | H | Me | 3 | H | H | —CO—⟨⟩—Br | 165–168 | | | M | 3 | 2 |
| 113 | Cl | H | H | Me | 3 | H | H | —CO—⟨⟩—CH₂Cl | 139–144.5 | | | M | 3 | 2 |
| 114 | Cl | Me | H | Me | 3 | H | H | —COOEt | 135–140 | 154–156 | 96–99 | S | 1 | 2 |
| 115 | Cl | H | H | Me | 3 | H | H | —COCH₂—⟨⟩ | 133–136 | | | M | 3 | 2 |
| 116 | Cl | H | H | Me | 3 | H | H | —CO—⟨naphthyl⟩ | 196–197 | | | M | 3 | 2 |
| 117 | Cl | H | H | Me | 3 | H | H | —COCH₂OEt | 147–149 | | | M | 3 | 2 |
| 118 | Cl | H | H | Me | 3 | H | H | —COC₃F₇ | 103–106 | | | M | 3 | 2 |
| 119 | Cl | H | H | Me | 3 | H | H | —CO—⟨⟩—SMe | 172–174 | | | M | 3 | 2 |
| 120 | Me | Me | H | Me | 3 | H | H | —COOEt | 133–137 | 179–181 | 185–190 | M | 3 | 2 |
| 121 | Cl | H | H | Et₂N | 3 | H | H | —COOEt | 127–142 | 179–181 | 185–190 | S | 4 | |
| 122 | Cl | H | H | Buⁱ | 3 | H | H | —COOEt | 108–113 | | | S | 4 | |

-continued

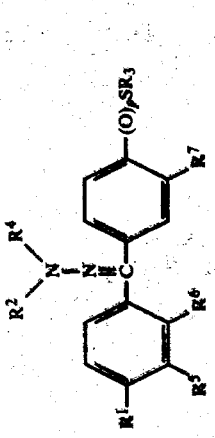

| Ex. No. | R¹ | R⁵ | R⁶ | R³ | p | R⁷ | R² | R⁴ | J | K | L | A | B | C |
|---|---|---|---|---|---|---|---|---|---|---|---|---|---|---|
| 123 | Cl | H | H | Me | 3 | H | H | —COCH₂Cl | 124–126 | | | M | 3 | 2 |
| 124 | Cl | H | H | Me | 3 | H | H | —CO—C₆H₄-CF₃ | 152–155 | | | M | 3 | 2 |
| 125 | Cl | H | H | Me | 3 | H | H | —CO—C₆H₄-Br | 144–150 | | | M | 3 | 2 |
| 126 | Cl | H | H | Me | 3 | H | H | —CO—cyclohexyl | 168–169 | | | M | 3 | 2 |
| 127 | Cl | H | H | Me | 3 | H | H | —CO—naphthyl | 104–106 | | | M | 3 | 2 |
| 128 | Cl | H | H | Me | 3 | H | H | —COCH=CHPh | 178–181 | | | M | 3 | 2 |
| 129 | Cl | H | H | Me | 3 | H | H | —CO—C₆H₃(Me) | 184–187.5 | | | M | 3 | 2 |
| 130 | Cl | H | H | Me | 3 | H | H | —CO—C₆H₄-Cl | 134.5–141 | | | M | 3 | 2 |
| 131 | Cl | H | H | Me | 3 | H | H | —COCH₂O—C₆H₄-F | 115–128 | | | M | 3 | 2 |
| 132 | Cl | H | H | Me | 3 | H | H | —COCH₂—C₆H₄-Br | 150–160 | | | M | 3 | 2 |
| 133 | Cl | H | H | Me | 3 | H | H | —COCH₂—C₆H₄-F | 162–163 | | | M | 3 | 2 |
| 134 | Cl | H | H | Me | 3 | H | H | —COCH=CH—C₆H₄-Cl | 196–198 | | | M | 3 | 2 |
| 135 | Cl | H | H | Me | 3 | H | H | —COCH₂O—C₆H₄-NO₂ | 172–176 | | | M | 3 | 2 |
| 136 | Cl | H | H | Me | 3 | H | H | —COCH₂OBu | 110–113 | | | M | 3 | 2 |
| 137 | Cl | H | H | Me | 3 | H | H | —COCH=CHCH₃ | 149–161 | 179–181 | | M | 3 | 2 |
| 138 | Cl | H | H | CH₃CH=CH | 3 | H | H | —COOEt | 154–158.5 | | 185–190 | S | 4 | 2 |

-continued

| Ex. No. | R¹ | R⁵ | R⁶ | R³ | p | R⁷ | R² | R⁴ | J | K | L | A | B | C |
|---|---|---|---|---|---|---|---|---|---|---|---|---|---|---|
| 139 | Cl | H | H | Bu$^s$ | 3 | H | H | —COOEt | 89–92 | 179–181 | 185–190 | S | 4 | |
| 140 | Cl | H | H | Me | 3 | H | H | —CO—⟨NMe₂⟩ | 216–219 | | | | 3 | 2 |
| 141 | Cl | H | H | Me | 3 | H | H | —COOCH₂C≡CH | 90–121 | | | T | 3 | |
| 142 | Cl | H | H | Me | 0 | H | H | —COOMe | 149.5–154.5 | 179–181 | 223–227 | T | 4 | |
| 143 | Cl | H | H | Pr | 0 | H | H | —COMe | 117–127 | 94–95 | 81–83 | N | 5 | |
| 144 | Cl | H | H | Pr | 0 | H | H | —COEt | 90–110 | 94–95 | 81–83 | T | 5 | |
| 145 | Cl | H | H | Pr$^i$ | 0 | H | H | —COOMe | 151–153 | 103–105 | oil | N | 7 | |
| 146 | Cl | H | H | Bu$^i$ | 0 | H | H | —COEt | 129–131 | 81–83 | | S | 5 | |
| 147 | Br | H | H | Pr$^i$ | 0 | H | H | —COOEt | 118–126 | 98–100 | | N | 7 | |
| 148 | Cl | H | Cl | Pr$^i$ | 0 | H | H | —COOEt | 138–140 | bp. 180-2/0.07 | | N | 5 | |
| 149 | Cl | H | H | Pr$^i$ | 3 | H | H | —COMe | 130–133 | 179–181 | 185–190 | S | 4 | |
| 150 | Cl | H | H | Ph | 3 | H | H | —COOEt | 113–127 | 179–181 | 185–190 | S | 4 | |
| 151 | Cl | H | H | Et | 0 | H | H | —COEt | 89–108 | oil | oil | M | 5 | |
| 152 | Br | H | H | Pr$^i$ | 0 | H | H | —COPr | 105–113. | 132–133.5 | oil | s | 5 | |
| 153 | Cl | H | H | Bu$^s$ | 0 | H | H | —COOEt | 95–124 | 94–95 | 81–83 | M | 5 | |
| 154 | Cl | H | H | Me | 0 | H | H | —COCH₂CH₂Cl | 113–120 | 94–95 | 81–83 | N | 7 | |
| 155 | Cl | H | H | Pr | 0 | H | H | —COCH₂Cl | 113–120 | 94–95 | 81–83 | M | 5 | |
| 156 | Cl | H | H | Pr | 0 | H | H | —CHO | 139–145 | 94–95 | 81–83 | M | 5 | |
| 157 | Cl | H | H | Pr$^i$ | 0 | H | H | —COPr$^i$ | 82–114 | 103–105 | bp. 188–90/0.1 | M | 5 | |
| 158 | Cl | H | H | Pr$^i$ | 0 | H | H | —COBu | 123–125 | 94–95 | 81–83 | M | 5 | |
| 159 | Cl | H | H | Pr$^i$ | 0 | H | H | —COBu$^i$ | 97–102 | 94–95 | 81–83 | M | 5 | |
| 160 | Cl | H | H | Pr$^i$ | 0 | H | H | —COC₆H₁₁ | 115–132 | 103–105 | bp. 188-90/01 | M | 5 | |
| 161 | Cl | H | H | Pr$^i$ | 0 | H | H | —COCHClCH₃ | 128–131 | 103–105 | bp. 188–90/0.1 | M | 5 | |
| 162 | Cl | H | H | Pr$^i$ | 0 | H | H | —COCH₂OMe | 97–103 | 103–105 | bp. 188–90/0.1 | N* | 5 | |
| 163 | Cl | H | H | Pr$^i$ | 0 | H | H | —CO—⟨OMe⟩ | 100–120 | 103–105 | bp. 188–90/0.1 | M | 5 | |
| 164 | Cl | H | H | Pr$^i$ | 0 | H | H | —COCH₂CHCl | 110–120 | 103–105 | bp. 188–90/0.1 | M | 5 | |
| 165 | Cl | H | H | Pr$^i$ | 0 | H | H | —COOEt | 115–135 | 103–105 | | s | 7 | |
| 166 | Cl | H | H | Pr | 0 | H | H | —COOMe | 120–141 | 94–95 | 81–83 | T | 7 | |
| 167 | Cl | H | H | Bu$^i$ | 0 | H | H | —COPr | 128.5–134 | 81–83 | oil | M | 5 | |
| 168 | Cl | H | H | Pr$^i$ | 0 | H | H | —COPr | 135–137 | 103–105 | bp. 188–90/0.1 | M | 5 | |
| 169 | Cl | H | H | Pr$^i$ | 0 | H | H | —COEt | 138–140 | 103–105 | bp. 188–90/0.1 | N | 5 | |
| 170 | Cl | H | H | Pr$^i$ | 0 | H | H | —COCH₂OPh | 112–125 | 103–105 | bp. 188–90/0.1 | N | 5 | |
| 171 | Cl | H | H | Pr$^i$ | 0 | H | H | —COMe | 146–149 | 103–105 | bp. 188–90/0.1 | N | 5 | |
| 172 | Cl | H | H | Pr$^i$ | 0 | H | H | —COPr | 146–147 | 103–105 | bp. 188–90/0.1 | M | 5 | |
| 173 | Cl | H | H | Pr$^i$ | 0 | H | H | —COBu | 137–139 | 103–105 | bp. 188–90/0.1 | N* | 5 | |
| 174 | Cl | H | H | Pr$^i$ | 0 | H | H | —CHO | 145–162 | 103–105 | bp. 188–90/0.1 | M | 5 | |

-continued

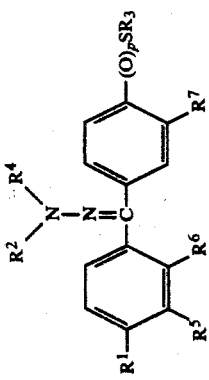

| Ex. No. | R¹ | R⁵ | R⁶ | R³ | p | R⁷ | R² | R⁴ | J | K | L | A | B | C |
|---|---|---|---|---|---|---|---|---|---|---|---|---|---|---|
| 175 | Cl | H | H | Pr$^i$ | O | H | H | —COPr$^i$ | 87–127 | 94–95 | 81–83 | M | 5 | |
| 176 | Cl | H | H | Pr$^i$ | O | H | H | | 90–140 | 94–95 | 81–83 | M | 5 | |
| 177 | Cl | H | H | Pr$^i$ | O | H | H | —CO-C₆H₄-Cl | 132–147 | 103–105 | bp. 188–90/0.1 | M | 5 | |
| 178 | Cl | H | H | Pr$^i$ | O | H | H | —CO-C₆H₄-Me | 88–91 | 103–105 | bp. 188–90/0.1 | M | 5 | |
| 179 | Cl | H | H | Pr$^i$ | O | H | H | —COC₈H₁₇ | 120–123 | 103–105 | bp. 188–90/0.1 | M | 5 | |
| 180 | Cl | H | H | Pr$^i$ | O | H | H | —CO-C₆H₄-Cl | 126–143 | 103–105 | bp. 188–90/0.1 | M | 5 | |
| 181 | Cl | H | H | Pr$^i$ | O | H | H | —COC₆H₁₃ | 111–122 | 103–105 | bp. 188–90/0.1 | M | 5 | |
| 182 | Cl | H | H | Pr$^i$ | O | H | H | —CO-C₆H₄-Cl | 130–144 | 103–105 | bp. 188–90/0.1 | M | 5 | |
| 183 | Cl | H | H | Pr$^i$ | O | H | H | —CO-furyl | 138–143 | 103–105 | bp. 188–90/0.1 | M | 5 | |
| 184 | Cl | H | H | Pr$^i$ | O | H | H | —COCHCl₂ | 121–126 | 103–105 | bp. 188–90/0.1 | M | 5 | |
| 185 | Cl | H | H | Pr$^i$ | O | H | H | —CO-cyclopropyl | 125–135 | 103–105 | bp. 188–90/0.1 | M | 5 | |
| 186 | Cl | H | H | Pr$^i$ | O | H | H | —COPh | 120–129 | 103–105 | bp. 188–90/0.1 | M | 5 | |
| 187 | Cl | H | H | Pr$^i$ | O | H | H | —CO-C₆H₄-OEt | 90–120 | 103–105 | bp. 188–90/0.1 | M | 5 | |
| 188 | Cl | H | H | Pr$^i$ | O | H | H | —COCH₂O-C₆H₄-OMe | 110–123 | 103–105 | bp. 188–90/0.1 | M | 5 | |
| 189 | Cl | H | H | Pr$^i$ | O | H | H | —COCH₂OEt | 98–123 | 103–105 | bp. 188–90/0.1 | M | 5 | |
| 190 | Cl | H | H | Pr$^i$ | O | H | H | —COCH(Me)OPh | 124–125 | 103–105 | bp. 188–90/0.1 | M | 5 | |
| 191 | Cl | H | H | Pr$^i$ | O | H | H | —CO-C₆H₃(OMe)₂ | 139–141 | 103–105 | bp. 188–90/0.1 | M | 5 | |
| 192 | Cl | H | H | Pr$^i$ | O | H | H | —COOpr | 100–105 | 103–105 | bp. 188–90/0.1 | M | 5 | |
| 193 | Cl | H | H | Pr$^i$ | O | H | H | —COSEt | 121–125 | 103–105 | bp. 188–90/0.1 | M | 5 | |

-continued

| Ex. No. | R¹ | R⁵ | R⁶ | R³ | p | R⁷ | R² | R⁴ | J | K | L | A | B | C |
|---|---|---|---|---|---|---|---|---|---|---|---|---|---|---|
| 194 | Cl | H | H | Pr$^i$ | 0 | H | H | —COPr$^i$ | 132–135 | 103–105 | bp. 188–90/0.1 | M | 5 | |
| 195 | Cl | H | H | Pr$^i$ | 0 | H | H | —COCH$_2$OPr | 120–127 | 103–105 | bp. 188–90/0.1 | M | 5 | |
| 196 | Cl | H | H | Pr$^i$ | 0 | H | H |  | 100–130 | 103–105 | bp. 188–90/0.1 | M | 5 | |
| 197 | Cl | H | H | Pr$^i$ | 0 | H | H | —COCH$_2$OBu | 98–102 | 103–105 | bp. 188–90/0.1 | M | 5 | |
| 198 | Cl | H | H | Pr$^i$ | 0 | H | H | —COCH$_2$CH$_2$OEt | 99–102 | 103–105 | bp. 188–90/0.1 | M | 5 | |
| 199 | Cl | H | H | Pr$^i$ | 0 | H | H | —COCH=CMe$_2$ | 115–120 | 103–105 | bp. 188–90/0.1 | M | 5 | |
| 200 | Cl | H | H | Pr$^i$ | 0 | H | H | —CO(CH$_2$)$_2$CH=CH$_2$ | 123–128 | 103–105 | bp. 188–90/0.1 | M | 5 | |
| 201 | Br | H | H | Pr$^i$ | 0 | H | H | —COPr | 106–125 | 98–100 | oil | M | 5 | |
| 202 | Br | H | H | Pr$^i$ | 0 | H | H |  | 144–146 | 98–100 | oil | M | 5 | |
| 203 | Br | H | H | Pr$^i$ | 0 | H | H | —COCH$_2$OEt | 102–106 | 98–100 | oil | M | 5 | |
| 204 | Br | H | H | Pr$^i$ | 0 | H | H | —COCH$_2$OMe | 95–108 | 98–100 | oil | M | 5 | |
| 205 | Me | H | H | Pr$^i$ | 0 | H | H | —COPr | 93–101 | 79–83 | bp. 180–84/0.1 | M | 5 | |
| 206 | Me | H | H | Pr$^i$ | 0 | H | H | —COPr$^i$ | 114–118 | 79–83 | bp. 180–84/0.1 | M | 5 | |
| 207 | MeO | H | H | Pr$^i$ | 0 | H | H | —COPr$^i$ | 90–110 | 69–71 | oil | M | 5 | |
| 208 | Cl | H | H | Bu$^i$ | 0 | H | H | —COPr | 141–144 | 81–83 | oil | M | 5 | |
| 209 | Cl | H | H | Bu$^i$ | 0 | H | H | —COBu | 122–127 | 81–83 | oil | M | 5 | |
| 210 | Cl | H | H | Pr$^i$ | 0 | H | H |  | 120–135 | 103–105 | | V | 7 | |
| 211 | Cl | H | H | Me | 3 | H | —COCH$_2$ | —COOCH$_2$ | 147–147.5 | | | M | 3 | 2 |
| 212 | Cl | together = benzo | H | Me | 3 | H | H | —COCH$_2$ | resin | | 142–3 | S | 4 | |
| 213 | Cl | H | H | Me | 3 | H | H | —COOEt | 130–138 | ND | 120–121 | W | 1 | |
| 214 | Cl | H | H | Me | 3 | H | H | together = N'N'-3-oxapentamethylene | 152–154 | 179–181 | 185–190 | X | 4 | |
| 215 | Cl | H | H | Me | 3 | H | H | —CSNH$_2$ | 152–162 | 179–181 | 185–190 | Y | 4 | |
| 216 | Cl | H | H | Me | 3 | H | H | —CONMe$_2$ | 175–180 | 179–181 | | P | 3 | |
| 217 | Cl | H | H | Me | 3 | H | H | —CONHPh | 145–150 | 181.5–182.5 | 140–140.5 | S | 1 | 2 |
| 218 | Cl | H | H | Me | 3 | H | H | — | 208–213 | | | MM | 3 | 2 |
| 219 | Cl | H | H | Me | 3 | H | H | —CO——Cl | 155–177 | | | NN | 3 | |
| 220 | Cl | H | H | Me | 3 | H | Me | —CONHEt | 113–175 | 142–143 | 98–99 | M | 3 | 2 |
| 221 | CF$_3$ | H | H | Me | 3 | H | H | —COOEt | 130–131 | | | S | 1 | * |

-continued

| Ex. No. | R¹ | R⁵ | R⁶ | R³ | p | R⁷ | R² | R⁴ | J | K | L | A | B | C |
|---|---|---|---|---|---|---|---|---|---|---|---|---|---|---|
| 222 | CF₃ | H | H | CF₃ | 3 | H | H | —COOEt | 123-124.5 | | 98-99 | S | 1 | |
| 223 | Cl | H | H | Me | 3 | H | H | —COCH=CH₂ | 145-146 | 142-143 | | M | 3 | 2 |
| 224 | Cl | H | H | Me | 3 | H | H | —CON⟨O⟩ | 159-162 | | 120-121 | Z | 1 | |
| 225 | Cl | H | H | Me | 3 | H | H | —COO—⟨⟩—⟨⟩ | 158-160 | | | M | 3 | 2 |
| 226 | Cl | H | H | Me | 3 | H | H | —COCF₃ | 115-115.5 | 179-181 | 57-60 | M | 3 | 2 |
| 227 | Cl | H | H | CF₃ | 3 | H | H | H | 84-99 | | | M | 2 | 2 |
| 228 | Cl | H | H | Me | 3 | H | H | —CO—⟨N⟩ | 178-181 | | | M | 3 | 2 |
| 229 | Cl | H | H | CF₃ | 3 | H | H | —CONH₂ | 165-171 | | | U | 1 | |
| 230 | Cl | H | H | CF₃ | 3 | H | H | —CONHMe | 190-192 | 179-181 | | O | 3 | 227 |
| 231 | Cl | H | H | Me | 3 | H | H | —COO—⟨⟩—Cl | 147-151 | | | M | 3 | 2 |
| 232 | Cl | H | H | CF₃ | 3 | H | H | —CO—⟨⟩—Cl | 170-174 | | | M | 3 | 227 |
| 233 | Cl | H | H | CF₃ | 3 | H | H | —CO—△ | 135-153 | | | M | 3 | 227 |
| 234 | Cl | H | H | Me | 3 | H | H | —COO—⟨⟩(Me)(Me) | 101.5-105.5 | | 57-60 | M | 3 | 2 |
| 235 | Cl | H | H | CF₃ | 3 | H | H | —COC₃H₇ | 137-143 | | | M | 3 | 227 |
| 236 | Cl | H | H | CF₃ | 3 | H | H | —COC₃H₇ⁱ | 142-145 | | | M | 3 | 227 |
| 237 | Cl | H | H | CF₃ | 3 | H | H | —COPs | 140-142 | | | M | 3 | 227 |
| 238 | Cl | H | H | CF₃ | 3 | H | H | —CHO | 130-134 | | | N' | 3 | 227 |
| 239 | Cl | H | H | Me | 3 | H | H | —CONHBuⁱ | 149 | | | OO | 3 | 2 |
| 240 | Cl | H | H | Me | 3 | H | H | —CONHBu | 180-187 | | | PP | 3 | 2 |

-continued

Structure: Diphenyl with R¹, R⁵, R³, R⁶, R⁷ substituents and N-N=C linkage with R², R⁴, (O)pSR₃

| Ex. No. | R¹ | R⁵ | R⁶ | R³ | p | R⁷ | R² | R⁴ | J | K | L | A | B | C |
|---|---|---|---|---|---|---|---|---|---|---|---|---|---|---|
| 241 | Cl | H | H | Me | 3 | H | H | —COCMe₂ | 119-121 | 179-181 | 120-121 | SS | 1 | |
| 242 | Cl | H | H | Me | 3 | H | H | —OMe —CONHiPr | 150-220 | | | QQ | 3 | 2 |
| 243 | Cl | H | H | Me | 3 | H | H | | 171-173 | | | N″ | 3 | 2 |
| 244 | Cl | H | H | Me | 3 | H | H | —COOH | 172-173 | | | TT | 1 | |
| 245 | Cl | H | H | Me | 3 | H | H | —COOCH₂CH₂OH | 177-179 | | | M | 3 | |
| 246 | Cl | H | H | Me | 3 | H | H | —COOCH₂CH₂Cl | 95-105 | | | UU | 1 | |
| 247 | Cl | H | H | CF₃ | 3 | H | H | —COC(OH)Me₂ | 118-121 | 179-181 | 120-121 | M | 3 | 2 |
| 248 | Cl | H | H | Me | 3 | H | H | —COOCH₂CH₂CN | 142-146 | 179-181 | 120-121 | VV | 1 | 227 |
| 249 | F | H | H | Me | 3 | H | H | together = pentamethylene | 170-176 | | | RR | 3 | |
| 250 | Buᵗ | H | H | Me | 3 | H | H | —CONHCH₂CH₂Cl | 148.5-152 | 169.5-171.5 | 110-111 | V | 1 | 2 |
| 251 | Cl | H | Cl | Me | 3 | H | H | —CONH₂ | 159-160 | 130-131 | 109-116 | S | 1 | |
| 252 | Cl | H | Cl | Me | 3 | H | H | —COOEt | 179-180 | | | M | 3 | 96 |
| 253 | Cl | H | H | CF₃ | 3 | H | H | —H | Oil | 134-135 | bp 161-2/0.7mm | WW | 1 | |
| 254 | Cl | H | H | Me | 3 | H | H | —COOCH₂CCl₃ | 96-97 | 179-181 | 120-121 | XX | 1 | |
| 255 | Cl | H | H | Me | 3 | H | H | —COCONH₂ | 170-175 | | | MA | 3 | 2 |
| 256 | Cl | H | H | Me | 3 | H | H | —COCH₂CH(OH)CH₃ | 139-141 | | | MB | 3 | 2 |
| 257 | Cl | H | H | Me | 2 | H | H | —COCOOEt | 135-139.5 | | | S | 1+ | |
| 258 | Cl | H | H | Me₂N | 3 | H | H | —COOEt | 142-150 | | | YY | 1 | |
| 259 | Cl | H | H | Me | 3 | H | H | —COOCH₂(CF₂)CF₃ | 152-153 | | 133-135 | MC | 3 | |
| 260 | Cl | H | H | Me | 3 | H | H | —COCH₂F | 157-159 | | | ZZ | 1 | 2 |
| 261 | Cl | H | H | Me | 3 | H | Me | together = 1-oxo-2-oxa-tetra-methylene | 140-141 | 179-181 | 120-121 | | | |
| 262 | Cl | H | H | Me | 3 | H | H | —COOCH₂CF₃ | 150-170 | 179-181 | 120-121 | SA | | |
| 263 | Cl | H | H | Me | 3 | H | H | —COO(CH₂)₂OCONHMe | 143-144 | | | O | 3 | 224 |
| 264 | Cl | H | H | Me | 3 | H | H | —CONHiPrʲ | 165-170 | | | MD | 3 | |
| 265 | Cl | H | H | Me | 3 | H | H | —CONHCOCCl₃ | 182 | | | ME | 3 | 2 |
| 266 | Cl | H | H | Me | 3 | H | H | —CONH₂ | 138-142 | 179-181 | 120-121 | SB | 1 | |
| 267 | Cl | H | H | Et₂N | 2 | H | H | —COOEt | 132-4 | 179-181 | 123-123 | S | 1+ | |

EXAMPLE 268

The product of Example 4 was separated into its geometric isomers by high pressure liquid phase chromatography. The E isomer had a m.p. of 160°–161° C. and the Z-isomer had a m.p. of 152°–156° C.

EXAMPLE 269

This Example illustrates the activity of compounds of the invention against larvae of the diamond back moth (*Plutella maculipennis*).

Ten larvae were placed in a tube together with a square inch of cabbage which had been dipped in the test solution and allowed to dry. After twenty-four hours untreated cabbage was added for food and after a further twenty-four hours an assessment was made of the mortality of the larvae.

Two replicates were carried out for each test compound and test solutions of varying concentrations employed so that an $LD_{50}$ value could be calculated.

The compounds of Examples 1 to 268 had an $LD_{50}$ of less than 5000 ppm.

EXAMPLE 270

The following types of concentrates were formulated as below:

| Water Dispersible Concentrate | |
| --- | --- |
| Product of Example 4 | 15.0% w/v |
| Ethylan BV[1] | 15.0% w/v |
| Ethylan C40 AH[2] | 15.0% w/v |
| Cyclohexanone | 30.0% w/v |
| N-Methylpyrrolidone | 31.0% w/v |
| Aqueous Flowable | |
| Product of Example 4 | 33.0% w/v |
| Dyapol PT[3] | 5.0% w/v |
| Monolan PB[4] | 0.25% w/v |
| Antifoam M30[5] | 0.5% w/v |
| Rhodopol 2% gel | 0.1% w/v |
| Water | to 100.0% vol |
| Oily Suspension | |
| Product of Example 4 | 33.0% w/v |
| Dyapol PT[3] | 1.0% w/v |
| Ethylan ENTX[7] | 15.0% w/v |
| Antimousse 411[8] | 0.5% w/v |
| Light Liquid Paraffin | to 100.0% vol. |
| Dispersible Powder | |
| Product of Example 4 | 50.0% w/v |
| Dyapol PT[3] | 10.0% w/v |
| Aerosol OT-B[9] | 0.5% w/v |
| Precipitated silica | 10.0% w/v |
| Polyviol M13/140[10] | 2.0% w/v |
| Kaolin | 27.5% w/v |

[1] A nonylphenolethoxylate.
[2] AH is an ethoxylated castor oil.
[3] Sodium salt of a cresol sulphonic acid/formaldehyde condensation product.
[4] Ethylene oxide/propylene oxide copolymer.
[5] A silicone based emulsion.
[6] A high molecular weight polysaccharide.
[7] Alkyl phenolethoxylate.
[8] A silicone based emulsion.
[9] Dioctyl ester of sodium sulphosuccinic acid.
[10] A grade of polyvinyl alcohol.

We claim:
1. Compounds of formula I

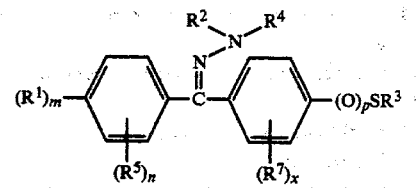

in which m is 0 and n is 0 or m is 1 and n is 0 or 1; p is 0 2 or 3, x is 0 or 1; $R^1$, $R^5$ and $R^7$ are halogen, alkyl, haloalkyl or alkoxy or $R^1$ and an adjacent $R^5$ group together with the benzene to which they are attached form a naphthyl group; $R^2$ and $R^4$ may be the same or different and are hydrogen; alkyl; an ester group of formula $R^8XCO$, where X is oxygen or sulphur and $R^8$ is selected from alkyl (optionally substituted by alkoxy, cycloalkyl, halogen, phenyl, substituted phenyl, naphthyl, phenoxy or substituted phenoxy), cycloalkyl, alkenyl, (optionally substituted by phenyl or substituted phenyl), alkynyl, phenyl, substituted phenyl, 2-naphthyl, furyl, thienyl, pyridyl, morpholinyl, piperidyl, and thiamorpholinyl; an acyl group of formula $R^9CO$ where $R^9$ is selected from hydrogen, alkyl, (optionally substituted by alkoxy, cycloalkyl, halogen, phenoxy or substituted phenoxy), cycloalkyl, alkenyl (optionally substituted by phenyl or substituted phenyl), alkynyl, phenyl, substituted phenyl, 2-naphthyl, morpholinyl, piperidyl and thiamorpholinyl; (wherein when one of $R^8$ or $R^9$ contains a substituted phenyl group, the phenyl is substituted by one or more groups selected from $C_{1-4}$ alkyl, $C_{1-4}$ haloalkyl, nitro, $C_{1-4}$ alkoxy, $C_{1-4}$ alkylthio, $C_{1-4}$ dialkylamino, phenyl and halogen); a carbamoyl group of formula $-CONR^{10}R^{11}$ where $R^{10}$ and $R^{11}$ are the same or different and are hydrogen or alkyl; or $R^2$ and $R^4$ together with the nitrogen to which they are attached form the group piperidine, pyrrolidine, thiamorpholine or morpholine; $R^3$ is alkyl, optionally substituted by halogen; alkenyl; N,N-dialkylamino; or phenyl, optionally substituted by alkyl or halogen; with the proviso that when p is 0, $R^2$ and $R^4$ are not both hydrogen.

2. Compounds according to claim 1, in which m is 1 and n is 0 and x is 0.

3. Compounds according to claims 1 in which $R^1$ is chlorine.

4. Compounds according to claim 1 in which p is 0 and at least one of $R^2$ and $R^4$ is an acyl or ester group.

5. Compounds according to claim 1 in which p is 3.

6. Compounds according to claim 5 in which $R^3$ is $C_{1-4}$ alkyl optionally substituted by halogen.

7. Compounds according to claim 5 in which $R^3$ is methyl or trifluoromethyl.

8. Compounds according to claim 1 in which $R^2$ is hydrogen and $R^4$ is not hydrogen.

9. Compounds according to claim 8 in which $R^4$ is of formula $R^8(O)_qCO$ where q is 0 or 1, $R^8$ is $C_{1-12}$ alkyl, optionally substituted by $C_{1-4}$ alkoxy, $C_{3-7}$ cycloalkyl, halogen, phenoxy or substituted phenoxy; $C_{3-7}$ cycloalkyl; $C_{2-12}$ alkenyl, optionally substituted by phenyl or substituted phenyl; $C_{2-6}$ alkynyl, or optionally substituted phenyl, wherein any substituted phenyl group is substituted by $C_{1-14}$ alkyl, $C_{1-4}$ haloalkyl, nitro, $C_{1-4}$ alkoxy, $C_{1-4}$ alkylthio, $C_{1-4}$ dialkylamino, phenyl or halogen; and when q is 0, R is also hydrogen.

10. A compound according to claim 1 selected from the group consisting of 4-chloro-4'-methylsulphonyloxybenzophenone formylhydrazone,
4-chloro-4'-methylsulphonyloxybenzophenone pentanoylhydrazone,
4-chloro-4'-methylsulphonyloxybenzophenone ethoxycarbonylhydrazone,
4-chloro-4'-methylsulphonyloxybenzophenone cyclopentylhydrazone,
4-chloro-4'-methylsulphonyloxybenzophenone 2,2-dimethylpropanoylhydrazone,
4-chloro-4'-methylsulphonyloxybenzophenone heptafluorobutyrylylhydrazone,
4-chloro-4'-methylsulphonyloxybenzophenone 4-chlorobenzoylhydrazone,
4-chloro-4'-methylsulphonyloxybenzophenone 3-chlorobenzoylhydrazone,
4-chloro-4'-methylsulphonyloxybenzophenone benzoylhydrazone,
4-chloro-4'-methylsulphonyloxybenzophenone 4-fluorobenzoylhydrazone,
4-chloro-4'-methylsulphonyloxybenzophenone 3-fluorobenzoylhydrazone,
4-chloro-4'-methylsulphonyloxybenzophenone 3,4-dichlorobenzoylhydrazone,
4-chloro-4'-methylsulphonyloxybenzophenone 4-trifluoromethylbenzoylhydrazone,
4-chloro-4'-trifluoromethylsulphonyloxybenzophenone ethoxycarbonylhydrazone,
4-chloro-4'-methylsulphonyloxybenzophenone 4-methylsemicarbazone,
4-bromo-4'-methylsulphonyloxybenzophenone semicarbazone,
4-chloro-4'-methylsulphonyloxybenzophenone semicarbazone,
4-chloro-4'-methylsulphonyloxybenzophenone isopropoxycarbonylhydrazone, and
4-chloro-4'-methylsulphonyloxybenzophenone phenoxycarbonylhydrazone.

* * * * *